(12) United States Patent
Boulais

(10) Patent No.: US 7,482,034 B2
(45) Date of Patent: Jan. 27, 2009

(54) EXPANDABLE MASK STENT COATING METHOD

(75) Inventor: Dennis R. Boulais, Danielson, CT (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 846 days.

(21) Appl. No.: 10/421,812

(22) Filed: Apr. 24, 2003

(65) Prior Publication Data

US 2004/0213893 A1    Oct. 28, 2004

(51) Int. Cl.
*A61L 33/00* (2006.01)
*B05D 3/00* (2006.01)

(52) U.S. Cl. ............... 427/2.1; 427/2.24; 427/2.25; 427/282; 427/300; 427/372.2

(58) Field of Classification Search ............ 427/2.1, 427/2.24, 2.25, 300, 372.2, 282
See application file for complete search history.

(56) References Cited

U.S. PATENT DOCUMENTS

| | | | | |
|---|---|---|---|---|
| 5,116,318 A | * | 5/1992 | Hillstead | 604/103.14 |
| 5,352,236 A | * | 10/1994 | Jung et al. | 606/194 |
| 5,395,651 A | * | 3/1995 | Sodervall et al. | 427/304 |
| 5,425,710 A | * | 6/1995 | Khair et al. | 604/103.05 |
| 5,679,400 A | * | 10/1997 | Tuch | 427/2.14 |
| 5,855,618 A | * | 1/1999 | Patnaik et al. | 424/423 |
| 6,368,658 B1 | | 4/2002 | Schwarz et al. | |
| 6,645,547 B1 | * | 11/2003 | Shekalim et al. | 427/2.24 |
| 2002/0017503 A1 | * | 2/2002 | Banas et al. | 219/69.11 |
| 2002/0160098 A1 | * | 10/2002 | Zamora et al. | 427/2.11 |
| 2003/0003220 A1 | | 1/2003 | Zhong et al. | |
| 2003/0083646 A1 | * | 5/2003 | Sirhan et al. | 604/891.1 |
| 2003/0199852 A1 | * | 10/2003 | Seward et al. | 604/533 |
| 2003/0215564 A1 | * | 11/2003 | Heller et al. | 427/2.25 |

FOREIGN PATENT DOCUMENTS

EP    1 329 230 A1    7/2003

* cited by examiner

*Primary Examiner*—Bret Chen
(74) *Attorney, Agent, or Firm*—Kenyon & Kenyon LLP

(57) ABSTRACT

A system and method for selective masking of stents using an expandable masking balloon to prevent deposition of therapeutic or protective coatings on portions of the stent during a coating application process. An expandable balloon is located within the inner region of a stent, the balloon is inflated until its outer surface contacts and the inner surface of the stent lattice in the areas in which the stent coating is not to be applied, thereby masking the stent inner surface from deposition of stent coating material during a stent coating process, and the coating is applied to the remaining exposed surfaces of the stent, for example by spraying or dipping the stent. The balloon is then deflated and removed from the coated stent. The balloon may be coated with, or formed from, a material impregnated with polytetrafluoroethylene to discourage adherence of the coating material to the balloon's outer surface in order to minimize coating waste and bridging of stent lattice openings by coating films.

10 Claims, 2 Drawing Sheets

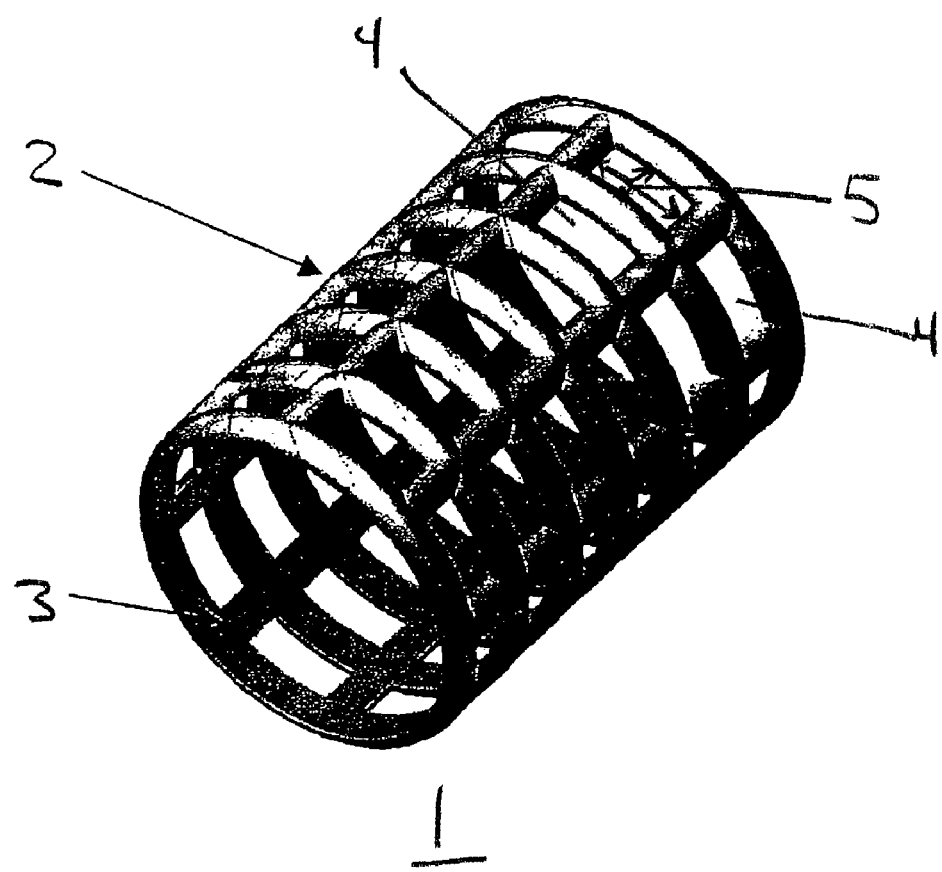

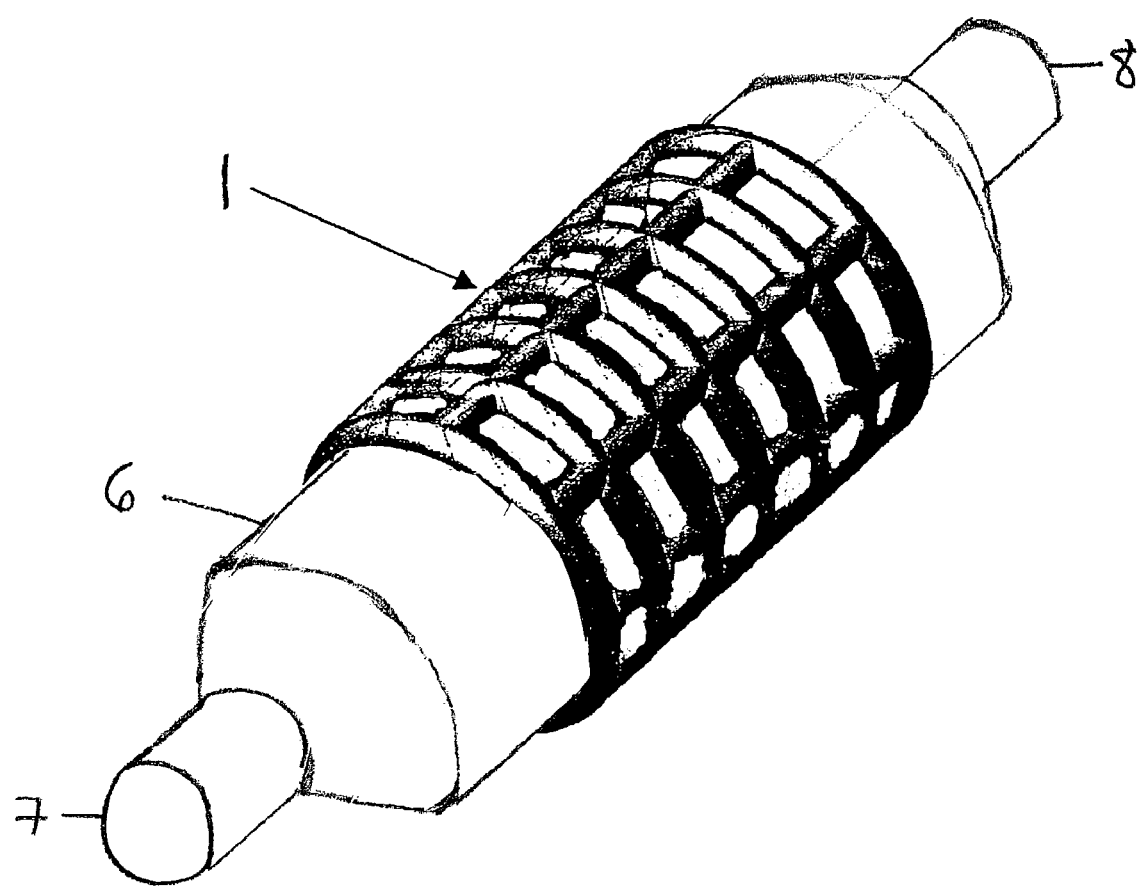

EXPANDABLE MASK STENT COATING METHOD

FIELD OF THE INVENTION

The present invention is directed to an improved method for applying therapeutic and protective coatings to stents. More specifically, the present invention pertains to a method for selective application of a coating to the outer surfaces of a stent while preventing the stent's interior surfaces receiving coating material.

BACKGROUND

Medical implants are used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been proposed or achieved using medical implants which both support a lumen within a patient's body and place appropriate coatings containing absorbable therapeutic agents at the implant location. Examples of such medical devices include catheters, guide wires, balloons, filters (e.g., vena cava filters), stents, stent grafts, vascular grafts, intraluminal paving systems, implants and other devices used in connection with drug-loaded polymer coatings. Such medical devices are implanted or otherwise utilized in body lumina and organs such as the coronary vasculature, esophagus, trachea, colon, biliary tract, urinary tract, prostate, brain, and the like.

The term "therapeutic agent" as used herein includes one or more "therapeutic agents" or "drugs". The terms "therapeutic agents" and "drugs" are used interchangeably herein and include pharmaceutically active compounds, nucleic acids with and without carrier vectors such as lipids, compacting agents (such as histones), virus (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Coatings used with the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

In a preferred embodiment, the polymer used to coat the medical device is provided in the form of a coating on an expandable portion of a medical device. After applying the drug solution to the polymer and evaporating the volatile solvent from the polymer, the medical device is inserted into a body lumen where it is positioned to a target location. In the case of a balloon catheter, the expandable portion of the catheter is subsequently expanded to bring the drug-impregnated polymer coating into contact with the lumen wall. The drug is released from the polymer as it slowly dissolves into the aqueous bodily fluids and diffuses out of the polymer. This enables administration of the drug to be site-specific, limiting the exposure of the rest of the body to the drug.

The polymer used in the present invention is preferably capable of absorbing a substantial amount of drug solution. When applied as a coating on a medical device in accordance with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2-0.3 microns and much thicker coatings, e.g., more than 10 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

The delivery of stents is a specific example of a medical procedure that may involve the deployment of coated implants. Stents are tube-like medical devices designed to be placed within the inner walls of a lumen within the body of a patient. Stents typically have thin walls formed from a lattice of stainless steel, Tantalum, Platinum or Nitinol alloys. The stents are maneuvered to a desired location within a lumen of the patient's body, and then typically expanded to provide internal support for the lumen. Stents may be self-expanding or, alternatively, may require external forces to expand them, such as by inflating a balloon attached to the distal end of the stent delivery catheter.

Where a stent is to be coated, care must be taken during its manufacture to ensure the coating is correctly applied and firmly adherent to the stent. When the amount of coating is insufficient or is depleted through stripping of poorly adherent coating during manufacture or deployment within the patient's body, the implant's effectiveness may be compromised, and additional risks may be inured into the procedure. For example, when the coating of the implant includes a therapeutic, if some of the coating were removed during deployment, the therapeutic may no longer be able to be administered to the target site in a uniform and homogenous manner. Thus, some areas of the target site may receive high quantities of therapeutic while others may receive low quantities of therapeutic. Similarly, if the therapeutic is ripped from the implant it can reduce or slow down the blood flowing past it, thereby, increasing the threat of thrombosis or, if it becomes dislodged, the risk of embolisms. In certain circumstances, the removal and reinsertion of the stent through a second medical procedure may be required where the coatings have been damaged or are defective.

The mechanical process of applying a coating onto a stent may be accomplished in a variety of ways, including, for example, spraying the coating substance onto the stent, so-called spin-dipping, i.e., dipping a spinning stent into a coating solution to achieve the desired coating, and electrohydrodynamic fluid deposition, i.e., applying an electrical potential difference between a coating fluid and a target to cause the coating fluid to be discharged from the dispensing point and drawn toward the target.

In these prior stent coating systems, the stents typically are coated on all surfaces. For example, with a coating spray application system, the relatively open lattice structure of the stent permits a coating spray to pass through the stent wall and coat the inner surfaces of the stent. Similarly, with a spin-dipping stent coating system, all the surfaces of the stent, interior and exterior, are exposed to the coating fluid upon immersion into the coating bath.

In the typical stent deployment, the outside surface of the stent contacts the vessel wall. Thus, ordinarily, only the outside surface of the stent needs to be coated. In certain instances, it may be desired that there is not significant exposure of the coating material to the bloodstream. Additionally or alternatively, it is desirable to coat only the outside surface of the stent to avoid excessive use of expensive coating agents and/or to leave the inside surface of the stent uncoated to minimize the risk of slippage on the delivery device.

Thus, there is a need for a system and method for applying a stent coating only on exterior surfaces of a stent, while preventing coating application on interior surfaces. Moreover, there is a need for a selective coating method that provides high quality coating of stents at high production rates.

SUMMARY OF THE INVENTION

The present invention is directed to a system and method for overcoming the foregoing disadvantages. Specifically, there is a provided a system and method in which an expandable balloon is placed within the inner region of a stent, the balloon is inflated until its outer surface contacts and thereby masks the inner surface of the stent lattice in the areas in which the stent coating is not to be applied, the coating is applied to the stent, for example by spraying or dipping the stent, while the inflated balloon inside the stent masks areas not to be coated, and the balloon is then deflated and removed from the coated stent.

The foregoing method is amenable to a number of variations. For example, the coating may be allowed to dry before the balloon is deflated, thereby minimizing the potential for wet coating to flow onto previously masked surfaces when the balloon is removed. Alternatively, the balloon may be immediately removed and the stent placed on a mandrel while the coating dries, thereby permitting the balloon to be more quickly made available for reuse. The balloon itself also may be made to resist adhesion of the coating on its outer surfaces, e.g., coated with or made from a material to which the coating does not adhere, in order to minimize or prevent "bridging" of the coating material across the openings in the stent lattice. Alternatively, the balloon may be encased in an expanding sleeve with similar coating repellant properties, such that when the balloon expands, the sleeve is pressed against the inner surface of the stent by the balloon to provide the desired masking. In a further embodiment, the balloon may be formed with raised projections that are designed to protrude through and fill the interstitial spaces in the stent lattice such that the balloon masks both the inner surface of the stent and the side faces of the stent lattice links in each lattice aperture. Even without such projections, the expansion of the balloon may be such that portions of the balloon pillow into the interstitial spaces to proving such masking.

The present invention thus provides the desired uniform stent coating on selected portions of the target stent while masking portions of the stent which are not to receive any coating material. The present invention does so in a manner well suited to high stent coating production rates.

BRIEF DESCRIPTION OF THE DRAWINGS

The foregoing and further objects, features and advantages of the invention will become apparent from the following description of preferred embodiments with reference to the accompanying drawings, wherein like numerals are used to represent like elements and wherein:

FIG. 1 is a perspective view of a typical stent to be coated in accordance with the method of the present invention.

FIG. 2 is a perspective view of the stent of FIG. 1 with an inflated masking balloon therein for masking an inner surface of the stent in accordance with the method of the present invention.

DETAILED DESCRIPTION

FIG. 1 illustrates a stent 1 which is to receive a coating of a therapeutic material. As shown in the figure, stent 1 is generally cylindrical in shape, and is in the form of a lattice of a material such as stainless steel, Tantalum, Platinum or Nitinol alloys. Stent 1 has an outer surface 2 that will contact the inner wall of a lumen such as a blood vessel (not shown), and thus is to be coated with a therapeutic coating material to be delivered to the lumen wall. The stent also has an inner surface 3 that will be in contact with the fluid carried by the lumen. Inner surface 3 is to be maintained coating-free. The lattice configuration of stent 1 provides interstitial openings 4. Facing these openings, the stent structure has lateral surfaces 5 between the outer surfaces and the inner surfaces.

The present method is not limited to the stent lattice configuration shown in FIG. 1, as any of a variety of well-known stent configurations may be used. The cross-sectional shape of the stent's links or structural members may also take any of a variety of known shapes. In the instance where the cross-sectional shape is round, it will be appreciated that the outer surface 2, the inner surface 3, and the lateral surfaces 5 represent general areas that need not be demarcated by a precise corner or other boundary line between the surfaces.

In the first step of the method in this embodiment, stent 1 is provided with a balloon 6 inserted into the stent. Balloon 6 may be constructed from a variety of elastic materials, preferably materials that can withstand large numbers of inflation/deflation cycles in a stent coating production environment.

In order to facilitate insertion and removal of the balloon, its outer diameter in the uninflated state is slightly smaller than the inner diameter of stent 1. After balloon 6 is inserted into stent 1, it may be inflated so that it expands radially until its outer surface contacts the inner surface of stent 1, as illustrated in FIG. 2. Either gas or hydraulic pressure may be applied to inflate balloon 6. In the present embodiment, air or fluid is supplied to balloon 6 via port 7 from a supply tube (not shown).

The end of the balloon opposite port 7 may be a closed end 8. Alternatively, end 8 may have a second open port leading into the balloon 6. While a second port is not required to perform the present method, a second port may provide production flexibility, permitting the air or fluid supply to balloon 6 to be shared simultaneously with additional inflatable masking balloons (not shown) in a multiple-stent coating production facility.

The inflation pressure applied to balloon 6 should be maintained sufficiently high to ensure the outer surface of the balloon maintains firm contact pressure against the inner surface 3 of the stent 1, thereby ensuring that the inner surface 3 of the stent is adequately masked when the stent coating is applied.

Once balloon 6 is inflated and masking the portions of stent 1 that are not to receive stent coating, the stent coating is applied. In this embodiment, the coating is applied by a coating spray dispenser while the stent is rotated within the coating spray to ensure that coating is applied to all the stent surfaces not masked by balloon 6. Alternatively, the spray dispenser may be rotated about stent 1, or the stent and inflated balloon combination may be inserted into a coating bath, as in the so-called "spin-dipping" stent coating process.

The stent coating may be permitted to dry on the stent with inflated balloon 6 in place. Once dry, balloon 6 may be deflated, permitting it to contract radially, freeing coated stent 1 for removal from the balloon. Alternatively, the stent be removed from the balloon prior to the complete drying of the newly-applied coating. In this alternative embodiment, balloon 6 is deflated prior to complete drying of the newly-applied coating, and coated stent 1 may be moved to a separate drying station, such as a drying mandrel (not illustrated).

A further embodiment of the present method provides additional masking of stent surfaces by the inflatable balloon in order to produce a coated stent with essentially no coating material exposed to bodily fluids once implanted in a patient. Specifically, in the step of providing an expandable masking balloon within an inner region of a stent, the balloon's design is tailored to fill the interstitial spaces 4 between the lattice links of the stent to be coated. One benefit of using a balloon with interstitial protrusions is that the protrusions minimize "bridging," or the formation of a film of coating material across the stent lattice openings, by physically blocking the formation of the coating film in the lattice openings. It will be appreciated by persons skilled in the art that even without protrusions, the balloon may be configured to "pillow" into the interstitial openings, providing a similar effect.

An additional embodiment of the present method employs the same balloon expansion step as the forgoing embodiments, with the addition of an expandable sleeve (not illustrated) between the outer surface of the balloon and the inner surface of the stent. Such a sleeve may be formed from a thin, flat sheet of material, such as Teflon-impreggnated material or Teflon-coated material, that is curled into a cylindrical shape with overlapping ends, where the diameter of the sleeve at rest is larger that the outer diameter of the uninflated balloon and smaller than the stent inner diameter. When the balloon is expanded in the inflating step, its outer surface presses radially outward on the sleeve, causing the sleeve diameter to increase as its overlapping ends slide over one another. The sleeve continues to expand until its outside surface contacts and masks the inner surface of the stent. When the deflating and removing step is performed, the sleeve ends slide over one another to permit the sleeve diameter to decrease and disengage from the coated stent. In order to ensure the entire inner surface of the stent is masked by the sleeve, it should be of sufficient length in the circumferential direction that its ends remain overlapping when expanded to its maximum diameter within the stent.

In each of the foregoing embodiments, it is preferred that the balloon or the sleeve discourage the adherence of the coating to their surfaces, both to discourage the formation of coating "bridging" between the stent lattice openings and to minimize the amount of costly stent coating material lost to application on surfaces other than the stent lattice. The repelling of coating material from the balloon or sleeve surfaces may be enhanced with materials that discourage the formation of films. In the foregoing embodiments, polytetrafluoroethylene (hereinafter referred to by the trademark name, Teflon), is employed. Specifically, the materials from which expandable masks are formed may be Teflon-impregnated. Alternatively, the balloon and sleeve may be provided with a Teflon coating to discourage coating adherence to the masks.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements. In addition, while the various elements of the disclosed invention are described and/or shown in various combinations and configurations, which are exemplary, other combinations and configurations, including more, less or only a single embodiment, are also within the spirit and scope of the present invention.

What is claimed is:

1. A method for applying a coating to a selected area of a stent, comprising the steps of:
    placing an expandable masking apparatus comprising an inflatable balloon and a coating repelling sleeve within an inner region of the stent, wherein the coating repelling sleeve comprises a sheet of material with ends of the coating repelling sleeve overlapping such that the coating repelling sleeve surrounds the inflatable balloon;
    inflating the inflatable balloon until an outer surface of the coating repelling sleeve contacts an inner surface of the stent at areas to be masked from coating, wherein the coating repelling sleeve has sufficient length in the circumferential direction that its ends remain overlapping when the balloon is inflated;
    applying a coating to the stent while the balloon is inflated; and
    deflating the balloon and removing the expandable masking apparatus from the stent.

2. The method of claim 1, wherein the masking apparatus repels the coating.

3. The method of claim 2, wherein the masking apparatus is treated with a coating repellant agent.

4. The method of claim 3, wherein the coating repellant agent is polytetrafluoroethylene.

5. The method of claim 2, wherein the masking apparatus is constructed of a coating repellant material.

6. The method of claim 5, wherein the coating repellant material is a polytetrafluoroethylene-impregnated polymer.

7. The method of claim 1, further comprising, prior to the step of deflating the balloon and removing the expandable masking apparatus from the stent, the step of:
    drying the coating on the stent.

8. The method of claim 1, further comprising, after the step of deflating the balloon and removing the expandable masking apparatus from the stent, the step of:
    transferring the coated stent to a coating drying station.

9. A method for applying a coating to a selected area of a stent, comprising the steps of:
    placing an expandable masking apparatus comprising an inflatable balloon and a coating repelling sleeve inside the stent;
    inflating the balloon until an outer surface of the expandable masking apparatus contacts an inner surface of the stent;
    applying a coating to the stent while the balloon is inflated; and
    deflating the balloon and removing the expandable masking apparatus from the stent.

10. The method of claim 9, wherein the coating repelling sleeve has polytetrafluoroethylene on an outer surface which contacts the inner surface of the stent.

* * * * *

UNITED STATES PATENT AND TRADEMARK OFFICE
CERTIFICATE OF CORRECTION

PATENT NO.        : 7,482,034 B2
APPLICATION NO.   : 10/421812
DATED             : January 27, 2009
INVENTOR(S)       : Dennis R. Boulais It is certified that error appears in the above-identified patent and that said Letters Patent is hereby corrected as shown below:

On the Title Page, Item (57) Abstract, line 6, "contacts and the" should be changed to --contacts the--;
Column 1, line 10, "surfaces receiving" should be changed to --surfaces from receiving--;
Column 1, line 37, "virus" should be changed to --viruses--;
Column 1, line 53, "viral, liposomes" should be changed to --viral liposomes--;
Column 2, line 9, "nitorfurantoin" should be changed to --nitrofurantoin--;
Column 2, line 11, "lisidomine" should be changed to --linsidomine--;
Column 2, line 17, "Warafin" should be changed to --warfarin--;
Column 2, line 19, "promotors" should be changed to --promoters--;
Column 2, line 21, "promotors" should be changed to --promoters--;
Column 2, line 65, "("BMP's")" should be changed to --("BMPs")--;
Column 3, line 2, "BMP's" should be changed to --BMPs--;
Column 3, line 8, "DNA's" should be changed to --DNAs--;
Column 4, line 5, "BAYHDROL®" should be changed to --BAYHYDROL®--;
Column 4, line 8, "collage" should be changed to --collagen--; and
Column 7, line 22, "impreggnated" should be changed to --impregnated--.

Signed and Sealed this

Twenty-third Day of March, 2010

David J. Kappos
*Director of the United States Patent and Trademark Office*